United States Patent
Soltanpour

(10) Patent No.: US 6,168,575 B1
(45) Date of Patent: Jan. 2, 2001

(54) METHOD AND APPARATUS FOR CONTROLLING INTRAOCULAR PRESSURE

(76) Inventor: David Pyam Soltanpour, 19A Addison St., Larchmont, NY (US) 10538

( * ) Notice: Under 35 U.S.C. 154(b), the term of this patent shall be extended for 0 days.

(21) Appl. No.: 09/015,759

(22) Filed: Jan. 29, 1998

(51) Int. Cl.$^7$ ................................................ A16M 5/00
(52) U.S. Cl. .................... 604/9; 359/600; 604/8; 604/119; 604/151; 415/13
(58) Field of Search .................... 604/149, 151, 604/119, 123, 131, 8, 9; 359/600; 415/13

(56) References Cited

U.S. PATENT DOCUMENTS

| | | | |
|---|---|---|---|
| 4,911,616 | * 3/1990 | Laumann, Jr. ................. | 417/413 |
| 5,062,841 | * 11/1991 | Siegel ................. | 604/891.1 |
| 5,171,213 | * 12/1992 | Price, Jr. ................. | 604/9 |
| 5,178,604 | * 1/1993 | Baerveldt et al. ................. | 605/8 |
| 5,326,345 | * 7/1994 | Price, Jr. ................. | 623/4 |
| 5,370,607 | * 12/1994 | Memmen ................. | 604/8 |
| 5,433,701 | * 7/1995 | Rubinstein ................. | 604/8 |
| 5,629,008 | * 5/1997 | Lee ................. | 424/426 |
| 5,676,679 | * 10/1997 | Simon et al. ................. | 606/170 |
| 5,681,275 | * 10/1997 | Ahmed ................. | 604/9 |
| 5,752,928 | * 5/1998 | De Roulhac et al. ................. | 604/8 |

* cited by examiner

Primary Examiner—Corrine McDermott
Assistant Examiner—Cheryl L. Huseman
(74) Attorney, Agent, or Firm—Alfred F. Hoyte, Jr.

(57) ABSTRACT

The present invention comprises a miniature pump which can be implanted in the eye for controllably removing excess fluid from the eye to treat glaucoma. The pump, in accordance with the inventive method, may be placed beneath the conjunctiva and/or extraocular muscles. In order to ensure that the right amount of fluid is removed from the eye the pump has a variable pumping rate, which results in a variable rate of removal of fluid from the eye. The pumping rate can be manually adjusted or automatically controlled in response to sensed ocular pressure. In the automatic mode, serious complications such as hypotony are avoided by reducing fluid flow when ocular pressure is low.

8 Claims, 2 Drawing Sheets

METHOD AND APPARATUS FOR CONTROLLING INTRAOCULAR PRESSURE

BACKGROUND OF THE INVENTION

1. Field of the Invention

The present invention relates to controlling ocular pressure. More specifically, it relates to an improved method and apparatus for controlling glaucoma.

2. Description of the Prior Art

As will be seen, the simplicity and effectiveness of my invention is not rivaled in the prior art.

U.S. Pat. No. 5,370,607 issued to Memmen discloses a glaucoma implant device which has a tubular shunt for draining fluid from the eye. By contrast, the present invention contemplates a controllable pumping mechanism for draining fluid from the eye to treat glaucoma.

U.S. Pat. No. 4,911,616 issued to Laumann, Jr. discloses a microminiature pump which may be used to administer medications in sensitive locations in the body such as the eye. The pump is programmable, but the application does not disclose which aspects of the pump operation can be controlled. By contrast, the present invention contemplates a miniature pump and conduit assembly which may be used to control glaucoma by controllably pumping fluid from the eye in accordance with sensed pressure conditions within the eye.

U.S. Pat. No. 5,062,841 issued to Siegel discloses an insulin pump which can be used to pump insulin directly into the bloodstream in response to blood glucose levels. By contrast, the present invention contemplates a miniature pump which can be implanted into the tissue surrounding the eye and can controllably reduce ocular pressure.

None of the above inventions and patents, taken either singly or in combination, is seen to describe the instant invention as claimed.

SUMMARY OF THE INVENTION

Briefly, the invention comprises a miniature pump which can be implanted in the eye for controllably removing excess fluid from the eye to treat glaucoma. The pump, in accordance with the inventive method, may be placed beneath the conjunctiva and/or extraocular muscles. In order to ensure that the right amount of fluid is removed from the eye the pump has a variable pumping rate, which results in a variable rate of removal of fluid from the eye. The pumping rate can be manually adjusted or automatically controlled in response to sensed ocular pressure. In the automatic mode, serious complications such as hypotony are avoided by reducing fluid flow when ocular pressure is low.

Accordingly, it is a principal object of the invention to provide a new and improved method and apparatus for controlling glaucoma.

It is a major object of this invention to provide an implantable pump assembly and associated method for controlling intraocular pressure.

It is another object of the invention to provide such a pump assembly having an automatically controlled pumping rate.

It is still another object of the invention to provide an improved, biologically implantable pump assembly having a pumping rate which is controllable in response to sensed local pressure conditions.

It is another object of the invention to provide an improved method and apparatus for controlling glaucoma including a micropump which is implanted into the anterior chamber of the eye.

It is yet another object of the invention to provide an improved, biologically implantable pump assembly having a draining tube which is relatively wide to disperse the outflow of fluid.

Finally, it is a general object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Referring now to FIGS. 1–4, a pump assembly, generally indicated by the numeral 10, is shown implanted in accordance with the method of the present invention. The pump 10 must be sufficiently small to be implanted in the eye without causing undue discomfort to the patient, and yet be able to store enough energy to pump fluid for a relatively long time. There are a few commercially available miniature pumps which meet this general criteria. In the preferred embodiment a Wilson Greatbatch Ltd. Model P65007 solenoid pump is used as the pump 10. The literature associated with this pump is hereby incorporated by reference. The pump is preferably about 5–15 millimeters long.

Figure 1:
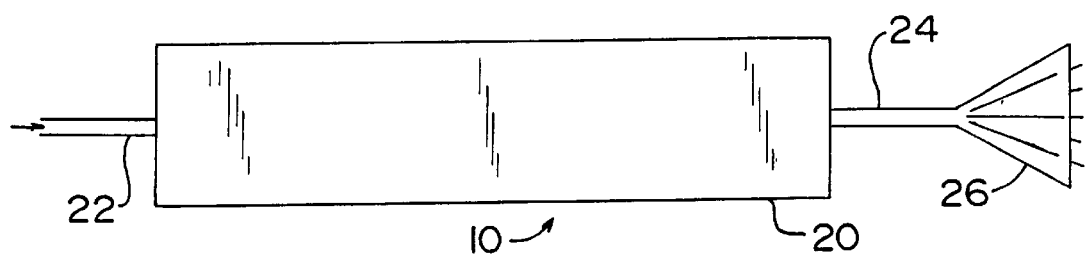
FIG. 1 is a top view of the pump assembly of the present invention.
Figure 3:
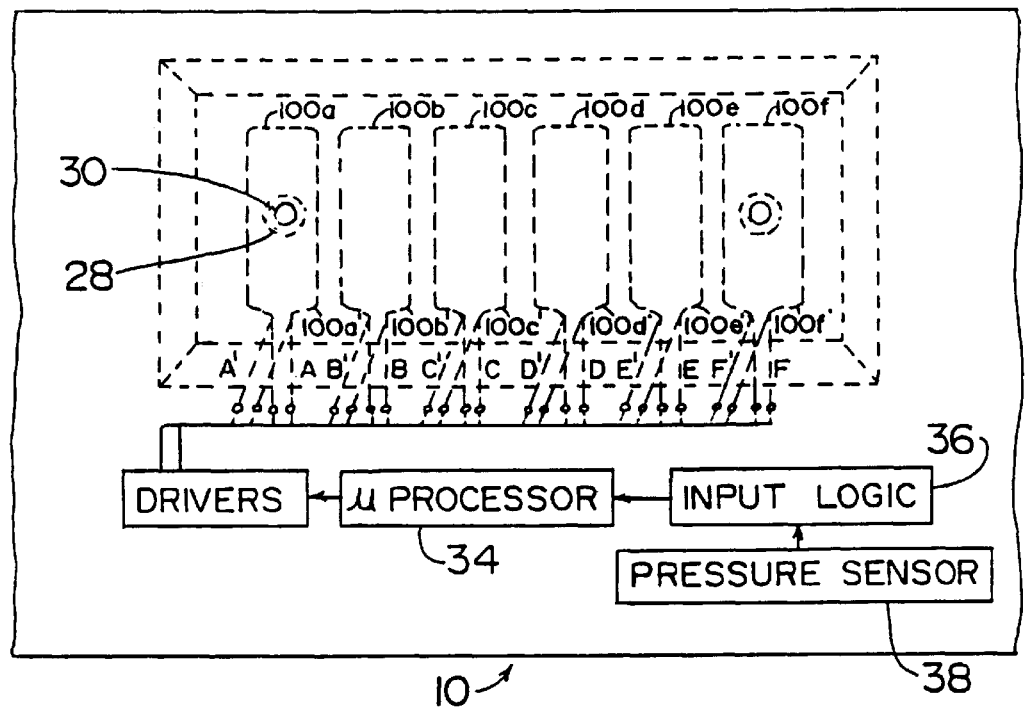
FIG. 3 is a top sectional view of the pump of FIG. 1 detailing the electronics.

Referring specifically to FIGS. 1 and 3, the pump 10, has a main body 20, which is made from biocompatible titanium or other biocompatible, corrosion resistant metal. Preferably, all of the parts of the pump in contact with bodily fluid are made from biocompatible titanium or other biocompatible, corrosion resistance metals. Also, the fluid flow path should be hermetically isolated from the solenoid coil and from the exterior of the pump. Of course, all of the electronics and the power source (not shown) must be contained within a hermetically sealed housing. The power source may be a small battery designed for long life. The pump 10 is designed to be driven by discharging a small value capacitor (about 25 $\mu F$) across a solenoid coil (not shown), which reciprocally operates a fluid displacement member or members (not shown) such as a piston.

The fluid displacement member operates to draw fluid into an intake conduit 22, into and through the main body 20 of the pump 10, and out through a drainage conduit 24 which has a fan shaped discharge end 26 to disperse the effluent fluid. The fan shaped end 26 helps to reduce the possibility of fibrosis. Accordingly, the possibility of occlusion of the drainage conduit 24 is reduced. Additionally, antifibroblastic agents may be applied after surgery to prevent fibrosis. It should be noted that the intake and drainage conduits 22, 24 must be of sufficient diameter to accommodate the required fluid flow. It can be readily appreciated that the constant fluid flow associated with the inventive method will help to keep the conduits free of blockage.

The pump 10 includes a check valve 28 at least at the intake 30 to allow for selectively limiting fluid flow. The rate of fluid flow is electronically controllable and is variable from 0 to about 10 $\mu$l per minute. In order to effectively control the rate of fluid flow or pumping rate, a microprocessor 34 and associated input logic 36 are operatively connected to the pump 10.

In the preferred embodiment, an active pumping action is employed. In order to effect such action, a pressure sensing device 38 must be employed. The pressure sensing device 38 is preferably small relative to the main body 20 of the pump 10 and is operatively connected to the microprocessor 34 for sending signals thereto. The pressure sensor 38 must be sufficiently sensitive to detect changes on the order of 1 mm Hg. Also, the pressure sensor 38 is preferably operated from the same power supply used to operate the pump. Thus, in accordance with the present invention, excessive ocular pressure is sensed, and the pump is activated at a rate which is determined by the sensed ocular pressure. One advantage of this method is that hypotony, due to excessive drainage of ocular fluid, is avoided, a common problem associated with prior art methods. To that end, if a pressure of less than 7 mm Hg is sensed the pump 10 can be shut off Alternatively, an external control mechanism (not shown) may be employed to manually control pump operation, when, e.g., the attending physician determines that the drainage rate is excessive.

Figure 2:
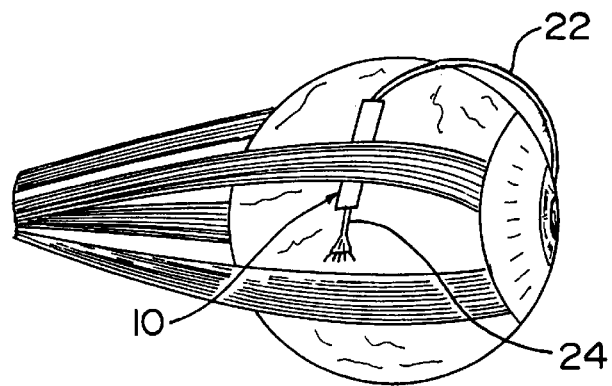
FIG. 2 is a side elevational view of a human eye upon which the device of the present invention has been implanted.
Figure 4:
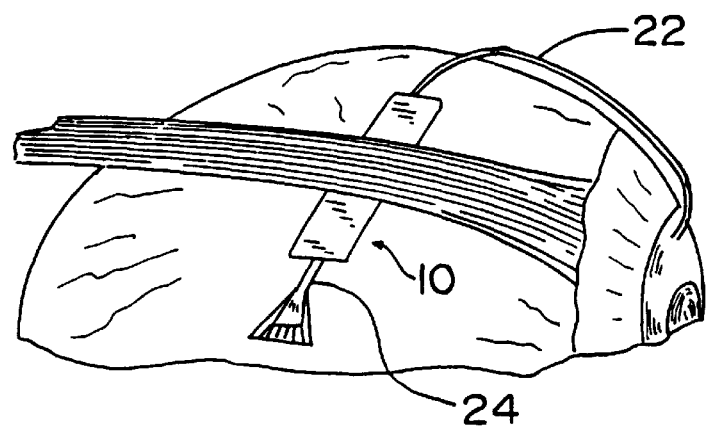
FIG. 4 is a close up elevational view of the implanted pump.

Placement of the pump 10 is illustrated in FIGS. 2 and 4. The main body 20 of the pump 10 may be placed under the extraocular muscles of the eye. The intake conduit 22 is placed to draw fluid from the anterior chamber of the eye, with the drainage conduit 24 being placed to discharge aqueous into the subconjunctival space.

In operation, after implantation of the device using standard surgical procedures, the pump 10 and sensor 38 will work in combination to monitor and control the immediate post operative eye pressure. Alternatively, a manual pressure sensor may be used and the pumping rate may also be adjusted manually as required.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

I claim:

1. A method of controlling glaucoma by implanting a miniature pumping device for draining aqueous humor out of the anterior chamber of the eye, wherein the device comprises a pumping means having a main body portion with an interiorly disposed flowpath, a control means fluidly isolated from the flowpath, an intake conduit connected within the main body portion at a connected end and fluidly coupled to said flowpath, said intake conduit having an intake end opposite said connected end, said intake end of the intake conduit positioned within the anterior chamber, and a discharge conduit connected within said main body portion at a connected end and fluidly coupled to said flowpath, said discharge conduit having an output end opposite said connected end, said output end of the discharge conduit positioned in the subconjunctival space, said method comprising the steps of:

implanting a miniature pump in or proximate the anterior chamber of the eye, in the subconjunctival space of the eye and securing it to the sclera of the eye, sensing the occular pressure of the eye, varying the pumping rate of said pumping means from 0 to about 10 microliters per minute in response to the sensed occular pressure.

2. A device to be surgically implanted in the eye for treating glaucoma by draining aqueous humor out of the anterior chamber of the eye comprising:

a miniature pump assembly for pumping said aqueous humor out of the anterior chamber, said pump assembly including pumping means having a main body portion with an interiorly disposed flowpath and including control means for controlling pumping rate, said control means fluidly isolated from said flowpath, an intake conduit connected within said main body portion at a connected end and fluidly coupled to said flowpath, said intake conduit having an intake end opposite said connected end, said intake end of the intake conduit positioned within the anterior chamber and a discharge conduit connected within said main body portion at a connected end and fluidly coupled to said flowpath, said discharge conduit having an output end opposite said connected end, said output end of the discharge conduit positioned in the subconjunctival space for draining the aqueous humor;

said control means capable of controlling the pumping rate to prevent excessive drainage of fluid from said anterior chamber.

3. The device of claim 2 wherein said discharge conduit has a first end for connection to said pump and an opposing end positioned to drain the aqueous into the subconjunctival space, said opposing end having a fan shaped tip.

4. The device of claim 2 wherein said control means includes a pressure sensing means operatively connected to a microprocessor, where said microprocessor is connected to a drive means for controlling the rate of fluid flow in response to the local pressure.

5. The device of claim 2 wherein said pumping means is made of biocompatible titanium.

6. The device of claim 4 wherein said rate of fluid flow is variable depending on the sensed intraocular pressure.

7. The device of claim 4 wherein said drive means can be manually controlled.

8. The device of claim 4 wherein said pressure sensing means is external to the eye.

* * * * *